US 6,521,249 B2

(12) United States Patent
Block et al.

(10) Patent No.: US 6,521,249 B2
(45) Date of Patent: Feb. 18, 2003

(54) FEEDSTOCK FOR PREPARTUM DAIRY CATTLE

(75) Inventors: Elliot Block, Yardley, PA (US); William K. Sanchez, Tigard, OR (US); Kenneth R. Cummings, Skillman, NJ (US)

(73) Assignee: Church & Dwight Co., Inc., Princeton, NJ (US)

( * ) Notice: Subject to any disclaimer, the term of this patent is extended or adjusted under 35 U.S.C. 154(b) by 0 days.

(21) Appl. No.: 09/814,910

(22) Filed: Mar. 22, 2001

(65) Prior Publication Data

US 2002/0176883 A1 Nov. 28, 2002

(51) Int. Cl.$^7$ .......................... A23K 1/165; A23K 1/17
(52) U.S. Cl. .................... 424/442; 424/400; 424/438; 424/439; 424/489; 426/74; 426/72; 426/807
(58) Field of Search .................. 424/400, 438, 424/439, 442, 489

(56) References Cited

U.S. PATENT DOCUMENTS

| 4,642,317 | A | | 2/1987 | Palmquist et al. |
| 5,264,227 | A | * | 11/1993 | Laroche et al. ............ 426/2 |
| 5,391,788 | A | | 2/1995 | Vinci et al. |
| 5,456,927 | A | | 10/1995 | Vinci et al. |
| 5,547,686 | A | | 8/1996 | Jenkins |
| 5,686,125 | A | * | 11/1997 | Mueller .................. 426/518 |
| 5,803,946 | A | | 9/1998 | Petcavich et al. |
| 5,874,102 | A | | 2/1999 | LaJoie et al. |

* cited by examiner

Primary Examiner—Thurman K. Page
Assistant Examiner—Charesse Evans
(74) Attorney, Agent, or Firm—Stephen B. Shear

(57) ABSTRACT

This invention provides a feedstock for controlling hypocalcemia in prepartum dairy cattle. An essential feature of the feedstock is a dietary cation-anion difference (DCAD) with a value between about −5 and +20 meq/100 g dietary DM. Other essential features are a weight ratio of potassium:magnesium between about 3-5:1, and between about 1-12 g/kg dietary DM of omega-6 fatty acid derivative having rumen-bypass properties.

18 Claims, No Drawings

FEEDSTOCK FOR PREPARTUM DAIRY CATTLE

CROSS-REFERENCE TO RELATED APPLICATION

The subject matter of this patent application is related to that disclosed in copending patent application Ser. No. 09/563,443, filed May 1, 2000; incorporated by reference.

BACKGROUND OF THE INVENTION

This invention generally relates to dietary factors with respect to prepartum dairy cattle nutrition. More specifically this invention relates to the effects of dietary cation-anion difference (DCAD) and essential fatty acid nutrients on calcium homeostasis in prepartum dairy cattle.

Metabolic problems with periparturient dairy cattle are numerous and interrelated. The majority of these problems involve subclinical and clinical hypocalcemia beginning from a few days prior to parturition through several days postpartum. This hypocalcemia, in the clinical form, is termed "milk fever" (parturient paresia) and manifests itself in cows with them becoming anorexic and, in its final stages, with cows having paralysis. While the onset of lactation is a precipitating factor for this disease, the root cause is the cow's inability to effectively regulate calcium metabolism via the hormonal cascade controlling bone calcium mobilization and deposition. Normally the blood serum of a dairy cow contains 9-12 mg of calcium per 100 ml. If the level decreases to about 5 mg per 100 ml, milk fever symptoms usually develop.

In its subclinical form, the hypocalcemia causes a cascade of disorders associated with muscle contraction, such as displaced abomasums and retained placentas. This subclinical hypocalcemia also leads to a reduced feed intake in the periparturient period. The reduced feed intake leads to the mobilization of body fat reserves and weight, which is known to be a causative factor in excess liver fat accumulation prior to the onset of lactation. Aside from the immediate veterinary costs associated with these disorders, there is a decided reduction in productivity for the remainder of the lactation.

Other dietary factors are of concern with respect to dairy cattle nutrition. Dietary macromineral elements are necessary for proper health and productive performance of lactating dairy cattle. As a class of nutrients, these elements have been the subject of extensive research, and considerable information exists about individual effects of each macromineral element. Information on interrelationships of macromineral elements in diets for lactating dairy cows, however, is relatively limited.

An early publication was the first to propose that mineral interrelations were related to acid-base status [J. Biol. Chem., 58, 235 (1922)]. It was proposed further that maintenance of normal acid-base equilibrium required excretion of excess dietary cations and anions. It was hypothesized that consumption of either excess mineral cations relative to anions or excess anions relative to cations resulted in acid-base disturbances in animals (A. T. Shohl. Mineral Metabolism. Reinhold Publishing Corp., New York. 1939).

Once animal nutritionists began to test this hypothesis, mineral interrelationships were found to affect numerous metabolic processes, and there was evidence that mineral interrelationships had profound influences. It was theorized that for an animal to maintain its acid-base homeostasis, input and output of acidity had to be maintained. It was shown that net acid intake was related to the difference between dietary cations and anions. The monovalent macromineral ions Na, K and Cl were found to be the most influential elements in the interrelationship (P. Mongin. Page 1, Third Ann. Int. Mineral Conf. Orlando, Fla. 1980).

Nutrient metabolism in animals results in the degradation of nutrient precursors into strong acids and bases. In typical rations fed to dairy cattle, inorganic cations exceed dietary inorganic anions by several milliequivalents (meq) per day. Carried with excess dietary inorganic cations are organic anions which can be combusted to $HCO_3^-$. Consequently, a diet with excess inorganic cations relative to inorganic anions is alkaline, and a diet with excess inorganic anions relative to cations is acidogenic.

Chloride is the most acidogenic element to be considered. An excess of dietary chloride can lead to a respiratory and/or metabolic acidosis. This is critical in ruminant nutrition because of salt (NaCl) feeding both in the diet and on an ad libitum basis. The acidogenic influence of chloride can be negated by sodium and potassium which are alkalogenic elements. Conversely, excess intake of sodium or potassium can induce metabolic alkalosis.

Blood pH ultimately is determined by the number of cation and anion charges absorbed in the blood. If more anions than cations enter the blood from the digestive tract, blood pH will decrease. It was proposed that a three-way interrelationship among dietary Na, K and Cl, i.e., the sum of Na plus K minus Cl [in meq per 100 g diet of dry matter (DM)], could be used to predict net acid intake. The term "dietary cation-anion difference (DCAD)" was coined to represent the mathematical calculation (W.K. Sanchez and D. K. Beede. Page 31, Proc. Florida Rum. Nutr. Conf. Univ. of Florida. 1991). Expressed in its fullest form, DCAD is written as follows:

$$\text{meq } [(Na^+ + K^+ + Ca^{+2} + Mg^{+2}) - (Cl^- + SO_4^{-2} + PO_4^{-3})]/100 \text{ g of dietary dry matter (DM)}.$$

A problem with including the multivalent macrominerals (Ca, Mg, P and S) in the DCAD expression for ruminants relates to the variable and incomplete bioavailability of these ions compared to Na, K and Cl. The expression employed most often in ruminant nutrition is the monovalent cation-anion difference:

$$\text{meq } (Na^+ + K^+ - Cl^-)/100 \text{ g dietary DM}$$

Because of the additional use of sulfate salts in prepartum rations, the expression that has gained most acceptance in ruminant nutrition is as follows:

$$\text{meq}(Na^+ + K^+) - (Cl^- + SO_4^{-2})/100 \text{ g dietary DM}$$

For a calculation, mineral concentration are first converted to milliequivalents:

$$\text{meq} - /100 \text{ g} = \frac{(\text{milligrams})/(\text{valence})}{(\text{g atomic weight})}$$

The following illustrates a calculation of the meq Na+K−Cl−S value of a diet with 0.18% Na, 1.0% K, 0.25% Cl and 0.2% S. There are 180 mg Na (0.18%=0.18 g/100 g or 180 mg/100 g), 1000 mg K (1.0% K), 250 mg Cl (0.25% Cl) and 200 mg S (0.2% S) per 100 g dietary DM. The $SO_4^-$ entity is calculated as atomic sulfur.

$$\text{meq Na} = \frac{(180 \text{ mg})(1 \text{ valence})}{(23 \text{ g atomic weight})} = 7.8 \text{ meq Na}$$

$$\text{meq K} = \frac{(1000 \text{ mg})(1 \text{ valence})}{(39 \text{ g atomic weight})} = 25.6 \text{ meq K}$$

$$\text{meq Cl} = \frac{(250 \text{ mg})(1 \text{ valence})}{(35.5 \text{ g atomic weight})} = 7.0 \text{ meq Cl}$$

$$\text{meq S} = \frac{(200 \text{ mg})(2 \text{ valence})}{(32 \text{ g atomic weight})} = 12.5 \text{ meq S}$$

The calculated DCAD value is as follows:

$$meq(\text{Na}+\text{K}-\text{Cl}-\text{S}) = 7.8+25.6-7.0-12.5 = 13.9 \text{ meq}/100 \text{ g dietary DM}$$

A simpler expression is as follows:

$$DCAD = (0.18\% \text{ Na}/0.023) + (1.0\% \text{ K}/0.039) - (0.25\% \text{ Cl}/0.0355) - (0.2\% \text{ S}/0.016) = +13.9 \text{ meq}/100 \text{ g dietary } DM$$

The macrominerals in a feedstock have other significant metabolic interrelationships relative to the health and performance of dairy cattle. Animal trials have indicated that a magnesium deficiency results in failure to retain potassium, which can lead to a potassium deficiency. Also, excessive levels of potassium interfere with magnesium absorption. Because sodium and potassium must be in balance, excessive use of salt depletes an animal's potassium supply (pages 99-104. Feeds & Nutrition. Second edition, Ensminger Publishing Co., 1990).

Clinical studies have provided evidence that magnesium is essential for keeping the intracellular potassium constant. Dietary deprivation of magnesium is accompanied by muscle potassium deficit despite an abundant supply of potassium. In animal studies, a diet depleted of potassium caused a significant hypokalemia and hypermagnesemia, a diuresis and natriuresis, a magnesiuria, and a decrease in the fecal excretion of magnesium (Chapter 12. Magnesium:lts Biological Significance. CRC Press, Inc., Boca Raton, Fla.).

An important aspect of the present invention relates to the inclusion of a lipid supplement in feedstocks for dairy cattle. Fatty acids are numbered from the carboxylic carbon atom. The position of double bonds is indicated by the Greek letter delta ($\Delta$) followed by the carbon number of the double bond. Linoleic acid is 18:2 omega-6$\Delta^{9,12}$. Arachidonic acid is 20:4 omega-6$\Delta^{5,8,11,4}$. Linolenic acid is 18:3 omega-3$\Delta^{9,12,15}$. The omega notation refers to the position of a double bond as an indicated number of carbon atoms from the terminal end of an unsaturated fatty acid.

Of particular interest are essential fatty acids with respect to lipid supplements in feedstocks. An "essential" fatty acid is one that cannot be synthesized by a ruminant de novo from precursors. It is necessary to include an essential fatty acid as an additive in a ruminant feedstock. Essential fatty acids include linoleic acid (omega-6), linolenic acid (omega-3) and arachidonic acid (omega-6).

There is continuing interest in the development of new methods and feedstocks for improving the health and productivity of dairy cattle.

Accordingly, it is an object of this invention to provide a method for controlling and minimizing metabolic malfunctions in dairy cattle.

It is another object of this invention to provide a feedstock with nutrient values which are adapted to control and prevent hypocalcemia in prepartum dairy cattle.

It is another object of this invention to provide a feedstock having a prescribed content of macromineral nutrients which are beneficial for the health and performance of prepartum dairy cattle.

It is another object of this invention to provide a feedstock having a prescribed weight ratio content of potassium and magnesium which is beneficial for the health and performance of prepartum dairy cattle.

It is a further object of this invention to provide a feedstock having a prescribed content of rumen-bypass essential fatty acid derivative which is beneficial for the health and performance of prepartum dairy cattle.

Other objects and advantages of the present invention shall become apparent from the accompanying description and example.

DESCRIPTION OF THE INVENTION

One or more objects of the present invention are accomplished by the provision of a feedstock for controlling hypocalcemia in prepartum dairy cattle which consists of a supplemented basal ration having a prescribed content of nutrients comprising (1) macromineral proportions as defined by a dietary cation-anion difference (DCAD) which corresponds to the equation:

$$DCAD = meq(\text{Na}^+ + \text{K}^+) - (\text{Cl}^- + \text{SO}_4^{-2})/100 \text{ g dietary } DM$$

where meq is milliequivalents, Na is sodium cations, K is potassium cations, Cl is chloride anions, $SO_4$ is sulfate anions, and DM is dry matter; wherein DCAD has a value between about -5 and +20 meq/100 g dietary DM; and wherein the feedstock has a weight ratio of potassium:magnesium between about 3-5:1; and (2) between about 1-12 g/kg dietary DM of omega-6 fatty acid derivative having rumen-bypass properties.

An important aspect of the present invention is a feed regimen for prepartum dairy cattle which has a prescribed content of macrominerals within a specified DCAD meq range, and has a specified potassium:magnesium weight ratio, and a specified content of omega-6 fatty acid derivative having rumen-bypass properties. An invention feedstock is effective for controlling and minimizing metabolic malfunctions in prepartum dairy cattle.

In another embodiment the present invention provides a method for controlling hypocalcemia in prepartum dairy cattle which comprises feeding a prepartum cow with a feedstock which consists of a supplemented basal ration having a prescribed content of nutrients comprising (1) macromineral proportions as defined by a dietary cation-anion difference (DCAD) which corresponds to the equation:

$$DCAD = meq(\text{Na}^+ + \text{K}^+) - (\text{Cl}^- + \text{SO}_4^{-2})/100 \text{ g dietary } DM$$

where meq is milliequivalents, Na is sodium cations, K is potassium cations, Cl is chloride anions, $SO_4$ is sulfate anions, and DM is dry matter; wherein DCAD has a value between about -5 and +20 meq/100 g dietary DM; and wherein the feedstock has a weight ratio of potassium:magnesium between about 3-5:1; and (2) between about 1-12 g/kg dietary DM of omega-6 fatty acid derivative having rumen-bypass properties.

In a typical invention feedstock, the weight ratio of potassium:magnesium is in the range between about 3.4-4.6:1.

Macrominerals can be selected from a group of compounds which include sodium bicarbonate, sodium carbonate, sodium sesquicarbonate, sodium chloride, sodium sulfate, sodium phosphate, potassium bicarbonate, potassium carbonate, potassium chloride, potassium sulfate, potassium phosphate, ammonium chloride, calcium chloride, magnesium chloride, magnesium sulfate, calcium sulfate, ammonium sulfate, and the like. Magnesium also can be provided by compounds such as magnesium oxide and magnesium hydroxide.

An essential feature of a present invention feedstock for control of hypocalcemia in prepartum dairy cattle is a prescribed content of omega-6 fatty acid nutrient having rumen-bypass properties.

Omega-6 fatty acid nutrient can be in the form of derivatives such as calcium and/or magnesium salts, and amide structures in which the amide nitrogen atom is substituted with hydrogen and/or aliphatic radicals. Fatty acid salts and amides are described in publications such as U.S. Pat. Nos. 4,642,317; 4,826,694; 5,391,788; 5,425,693; 5,456,927; 5,496,572; 5,547,686; 5,670,191; 5,874,102; and the like, incorporated by reference.

Omega-6 fatty acids are illustrated by polyunsaturated long chain alkenoic compounds such as linoleic acid (18:2), gamma-linolenic acid (18:3), arachidonic acid (20:4), adrenic acid (22:4), tetracosatetraenoic acid (24:4), tetracosapentaenoic acid (24:5) and docosapentaenoic acid (22:5).

A feedstock of the present invention preferably has a specified content of rumen-bypass essential omega-6 fatty acid nutrient comprising linoleic acid and/or arachidonic acid derivative.

The rumen-bypass properties of the omega-6 fatty acid nutrient in a feedstock is essential, in order to minimize biohydrogenation of the omega-6 fatty acid derivative under rumen-incubation conditions. Biohydrogenated fatty acids are not effective for control of hypocalcemia in prepartum dairy cattle.

A present invention feedstock normally is fed to prepartum dairy cattle at a rate between about 8-12 Kg DM/cow/day. The rate of feeding provides between about 20-100 g/cow/day of rumen-bypass essential omega-6 fatty acid derivative in the cow intestine.

Prog. Lipid Res., 36 (No. 2-3), 131 (1997) is a review article describing the effects of various essential fatty acids on relevant aspects of pathophysiology.

Essential fatty acids such as linoleic acid induce elevation of intracellular free calcium anions by calcium anion mobilization [Biochem. Med. Metab. Biol., 51(2), 166(1994)].

A nutrient supplemented feedstock of the present invention includes a basal ration of the type formulated for dairy cattle. Suitable basal rations are described in publications such as J. Dairy Sci., 77, 1437(1994): 77, 1661(1994); and 77, 3096 (1994); incorporated by reference.

A typical feedstock will include silage, and energy concentrate and protein concentrate. A basal feedstock can comprise 6.4 kg corn silage (35% dry matter), 17 kg alfalfa silage (50% dry matter), 1 kg alfalfa hay, and 6.9 kg energy and 2.1 kg protein concentrate.

The compositions of an energy concentrate and a protein concentrate are illustrated in TABLE I.

TABLE I

| | Weight, % |
|---|---|
| ENERGY CONCENTRATE | |
| Ground shelled corn | 56.87 |
| Ground ear corn | 34.50 |

TABLE I-continued

| | Weight, % |
|---|---|
| Molasses | 2.00 |
| Animal/vegetable fat | 1.00 |
| Minerals and vitamins | 5.63 |
| PROTEIN CONCENTRATE | |
| Soybean meal - 44% | 60.88 |
| Soybran hulls | 26.20 |
| Molasses | 1.00 |
| Fish meal | 3.90 |
| Animal/vegetable fat | 1.00 |
| Sodium bicarbonate | 3.90 |
| Magnesium oxide | 0.92 |

One or more other ingredients can be incorporated in a present invention feedstock composition, such as biologically active derivatives.

An optional biologically active ingredient can be included in a feedstock in an effective quantity between about 0.05-20 weight percent, based on the weight of feedstock. It can be selected from a broad variety of nutrients and medicaments, either as a single component or as a mixture of components, which are illustrated by the following listing of active species:

1. sugars and complex carbohydrates which include both water-soluble and water-insoluble monosaccharides, disaccharides and polysaccharides.

Cane molasses is a byproduct from the extraction of sucrose from sugar cane. It is commercially available at standard 79.5° Brix concentration, which has a water content of about 21 weight percent, and a sugar content of 50 weight percent. Sugar beet byproducts also are available as low cost carbohydrate sources.

Whey is a byproduct of the dairy industry. The whey is a dilute solution of lactalbumin, lactose, fats, and the soluble inorganics from milk. Dried whey solids typically have the following composition:

| Protein | 12.0% |
|---|---|
| Fat | 0.7% |
| Lactose | 60.0% |
| Phosphorus | 0.79% |
| Calcium | 0.874% |
| Ash | 9.7% |

Another source of carbohydrate is derived from the pulp and paper industry which produces large quantities of byproduct lignin sulfonates from wood during the sulfite pulping process. The carbohydrate byproduct is a constituent of the spent sulfite liquor.

2. aminoacid ingredients either singly or in combination which include arginine, histidine, isoleucine, leucine, lysine, methionine, phenylalanine, threonine, tryptophan, valine, tyrosine ethyl HCl, alanine, aspartic acid, sodium glutamate, glycine, proline, serine, cysteine ethyl HCl, and the like, and analogs and salts thereof.

3. vitamin ingredients either singly or in combination which include thiamine HCl, riboflavin, pyridoxine HCl, niacin, niacinamide, inositol, choline chloride, calcium pantothenate, biotin, folic acid, ascorbic acid, vitamin $B_{12}$, p-aminobenzoic acid, vitamin A acetate, vitamin K, vitamin D, vitamin E, and the like.

Trace element ingredients include compounds of cobalt, copper, manganese, iron, zinc, tin, nickel, chromium, molybdenum, iodine, silicon, vanadium and selenium.

4. protein ingredients as obtained from sources such as dried blood or meat meal, dried and sterilized animal and poultry manure, fish meal, liquid or powdered egg, fish solubles, cell cream, soybean meal, cottonseed meal, canola meal, and the like. Protein ingredients include non-protein nitrogen compounds such as urea, biuret, ammonium phosphate, and the like.
5. antioxidants as illustrated by butylated hydroxyanisole, butylated hydroxytoluene, tocopherol, tertiary-butylhydroquinone, propyl gallate, and ethoxyquin; and suitable preservatives include sodium sorbate, potassium sorbate, sodium benzoate, propionic acid, α-hydroxybutyric acid, and the like.
6. suspension stabilizing agents which preferably are selected from nonionic surfactants, hydrocolloids and cellulose ethers. These types of chemical agents are illustrated by polyethylene oxide condensates of phenols, $C_8$-$C_{22}$ alcohols and amines; ethylene oxide reaction products with fatty acid partial esters of hexitans; alkylarylpolyoxyethylene glycol phosphate esters; gum arabic; carob bean gum; tragacanth gum; ammonium, sodium, potassium and calcium alginates; glycol alginates; xanthan gum; potato agar; alkylcellulose; hydroxyalkylcellulose; carboxyalkylcellulose; and the like.

The feedstock initially is metabolized in the rumen of cattle and other ruminants. The rumen contains microorganisms, such as bacteria and protozoa, which break down complex compounds ingested by the animal via a fermentation process.

The present invention further contemplates a dietary supplement for incorporation in ruminant feedstock for control of hypocalcemia in prepartum dairy cattle, wherein the supplement is formulated to provide macromineral cations and anions and omega-6 fatty acid derivative in calculated proportions in a basal ration, whereby the resultant macromineral and omega-6 fatty acid derivative specifications meet the requirements of a feedstock in accordance with the present invention. The dietary supplement facilitates formulation of dairy cattle feedstocks with target DCAD, and required K:Mg ratio and omega-6 fatty acid derivative content.

A dietary supplement can be in the form of powder, granules, pellets, or the like. A supplement can contain other ingredients such as a binder, or an active agent such as nonprotein nitrogen.

A dietary supplement of the present invention can have correspondence with the following illustrated nutrient contents, and can include other ingredients to satisfy customized formulation requirements.

| Dietary Supplements | |
|---|---|
| Ingredient | Parts by Weight |
| Chloride-containing | 10–30 |
| Sulfur-containing | 0–50 |
| Magnesium-containing | 5–30 |
| Omega-6 fatty acid derivative-containing | 50–120 |

In a further embodiment, a dietary supplement can have controlled-release properties. This is illustrated by a supplement which is composed of coated particles of a core matrix of nutrients which comprise the above described anions, cations and omega-6 fatty acid ingredient weight contents. A nonprotein nitrogen ingredient such as urea can be included in a quantity up to about 80 weight percent of the core matrix of the coated particles. The coating can be of the type described in publications such as U.S. Pat. No. 3,413,118 and U.S. Pat. No. 5,803,946; incorporated by reference. A selected coating, such as polyvinyl acetate, has rumen-degradable properties.

The following Example is further illustrative of the present invention. The components and specific ingredients are presented as being typical, and various modifications can be derived in view of the foregoing disclosure within he scope of the invention.

EXAMPLE

This Example illustrates ruminant feedstocks and a feeding regimen for control of hypocalcemia in prepartum dairy cattle in accordance with the present invention.

A.

Sixty mature Holstein cows at the end of their second lactation are assigned to one of three dietary treatment groups: 1) control; 2) negative DCAD; 3) control plus a prepartum rumen bypass fatty acid supplement. Treatments are fed from 28 days prepartum until parturition. After calving, all cows are fed the same diet.

Diets are formulated to meet or exceed National Research Council nutrient requirements for prepartum cows. Nutrient composition of the three diets is as follows:

| Nutrient | Transition Prepartum | | |
|---|---|---|---|
| | 1 | 2 | 3 |
| Net Energy Lactation (Mcal/kg) | 1.55 | 1.55 | 1.55 |
| Neutral Detergent Fiber (%) | 35 | 35 | 35 |
| Non-Fiber Carbohydrates (%) | 34 | 34 | 34 |
| Total Fat (%) | 4 | 4 | 4 |
| Added Fat (%) | 2 | 2 | 2 |
| Crude Protein (CP) (%) | 15 | 15 | 15 |
| Undegradable Intake Protein (% of CPI) | 35 | 35 | 35 |
| Degradable Intake Protein (% of CPI) | 10 | 10 | 10 |
| Dietary Cation Anion Difference, DCAD (Na + K) – (Cl + S)/(meq/100 g DM) | 20 | –10 | 20 |
| Calcium (%) | 1.2 | 1.2 | 1.2 |
| Phosphorus (%) | .4 | .4 | .4 |
| Magnesium (%) | .4 | .4 | .4 |
| Potassium (%) | 1.6 | 1.6 | 1.6 |

All diets contain corn silage, mixed grass-legume haylage, corn grain, soybean meal, and distiller's grain. Diets 1 and 2 have the added fat in the form of 5 tallow, and diet 3 has the fat added in the form of the prepartum Megalac supplement (Church & Dwight). The DCAD of diets 1 and 3 are achieved through normal mineral supplementation, and for diet 2 by the addition of the chloride salts of magnesium and calcium. Similar magnesium and calcium concentrations are achieved in diets 1 and 3 by using magnesium oxide and calcium carbonate.

Prepartum Megalac is a commercial calcium salt of fatty acids supplement designed to achieve rumen bypass of the fatty acids. The major fatty acids constituents of this supplement are linoleic acid (47%), oleic acid (20%), palmitic acid (14%), linolenic acid (4%), and other fatty acids (15%).

Diets are offered to cows beginning at 28 days prepartum as total mixed rations twice daily until parturition. At parturition cows are switched onto a standard postpartum diet and monitored for the next 15 weeks.

Measurements in the prepartum period are: daily dry matter intake (DMI); daily blood total and ionized calcium, non-esterified fatty acids, beta hydroxybutyric acid and glucose; total liver fat at 28, 7 and 1 day prepartum via liver biopsy; urinary pH at 28, 7 and 1 day prepartum. Measurements in the postpartum period are: Daily DMI and milk production; weekly milk composition; blood total and ionized calcium, non-esterified fatty acids, beta hydroxybutyric acid and glucose on days 1 postpartum and each 7 days after that time; total liver fat on day 1, 7 and 28 postpartum via liver biopsy. Disease incidence is recorded.

Results

Prepartum Measurements

Daily DMI are significantly different (P<.05) between diets. Diet 2 has the lowest overall DMI (7 kg/cow/day) followed by Diet 1 (9 kg/cow/day) while Diet 3 has elicited the highest DMI (11 kg/cow/day). All cows decline in DMI in the 7 days immediately prior to parturition; however, cows offered Diet 3 decline the least (P<0.05) compared to the other two diets.

Total and ionized blood calcium concentration are different among cows offered the three diets (P<0.05). An average concentration of blood Ca over the entire feeding period prepartum shows that blood total and ionized Ca is highest for cows offered diets 2 and 3 with no difference between the two groups, and cows offered diet 1 have the lowest values. All cows decline in total and ionized blood Ca 1s in the 7 days prepartum with the most precipitous decline in the last 2 days prepartum. Again, blood total and ionized Ca are highest for cows offered diets 2 and 3 with no difference between the two groups, and cows offered diet 1 have the lowest values (P<0.05).

Blood beta hydroxybutyrate and non-esterified fatty acid concentrations are lowest (P<0.05) and glucose highest (P<0.05) for cows offered Diet 3 throughout the prepartum period with the differences being exaggerated as day of calving approached. Liver biopsies reveal that all cows have similar liver fat levels at 28 days prepartum (P>0.05) but cows offered Diet 3 have significantly (P<0.05) less liver triglycerides at days 7 and I prepartum compared with Diets 1 and 2. Urinary pH is similar for all cows at 28 days prepartum, but is significantly lower (P<0.05) for cows offered Diet 2 at 7 and 1 days prepartum.

Postpartum Measurements

DMI is higher (P<0.05) for cows offered Diet 3 prepartum each day from calving through day 40 postpartum; with cows offered Diet 2 prepartum being intermediate (P<0.05); and cows offered Diet 1 prepartum being the lowest. Start-up and daily milk production follows the same pattern as DMI with cows offered Diet 1 prepartum having the lowest values (P<0.05), and cows offered Diet 3 prepartum 10 having the highest (P<0.05) values.

Total and ionized calcium in blood are highest (P<0.05) for cows offered Diets 2 and 3 prepartum for the first 4 days postpartum. After that time no differences are detected. Blood betahydroxybutyrate and non-esterified fatty acids are lowest (P<0.05) and glucose highest (P<0.05) for cows offered Diet 3 prepartum for the first 4 weeks postpartum. From week-4 to the end of the trial there are no differences in these parameters between cows offered Diets 2 and 3 prepartum. However, cows offered Diet 1 prepartum always have lower (P<0.05) values for glucose and higher values (P<0.05) for beta hydroxybutyrate and non-esterified fatty acids than the other 20 cows. Liver triglyceride content is always less (P<0.05) for cows offered Diet 3 prepartum.

The incidence of metabolic diseases are as follows for cows offered Diets 1, 2, and 3, respectively: For milk fever (clinical hypocalcemia) 8/20, 3/20, and 1/20; for subclinical hypocalcemia between day 1 prepartum to day 3 postpartum 18/20, 7/20, and 2/20; clinical bovine ketosis 5/20, 4/20, and 0; displaced abomasums 2/20, 2/20 and 0/20.

B.

In accordance with present invention, the following type of dietary blends facilitate formulation of feedstocks for prepartum dairy cattle:

|  | Parts by Weight | | | Range |
|---|---|---|---|---|
| Calcium chloride | 30 | 15 | 10 | (10–30) |
| Magnesium sulfate | 15 | 10 | 5 | (5–30) |
| Linoleic acid amide and/or arachidonic acid amide* | 55 | 75 | 85 | (50–120) |

*similar results with calcium and/or magnesium salt derivative.

What is claimed is:

1. A feedstock for controlling hypocalcemia in prepartum dairy cattle which comprises a supplemented basal ration having a prescribed content of nutrients comprising (1) macromineral proportions as defined by a dietary cation-anion difference (DCAD) which corresponds to the equation:

$$DCAD = meq(Na^+ + K^+) - (Cl^- + SO_4^{-2})/100 \text{ g dietary } DM$$

where meq is milliequivalents, Na is sodium cations, K is potassium cations, Cl is chloride anions, $SO_4$ is sulfate anions, and DM is dry matter; wherein DCAD has a value between about −5 and +20 meq/100 g dietary DM; and wherein the feedstock has a weight ratio of potassium:magnesium between about 3-5:1; and (2) between about 1-12 g/kg dietary DM of omega-6 fatty acid derivative having rumen-bypass properties.

2. A feedstock in accordance with claim 1 wherein the weight ratio of potassium:magnesium in the feedstock is between about 3.4-4.6:1.

3. A feedstock in accordance with claim 1 wherein the DCAD macrominerals are selected from the group consisting of sodium bicarbonate, sodium carbonate, sodium sesquicarbonate, sodium chloride, sodium sulfate, sodium phosphate, potassium bicarbonate, potassium carbonate, potassium chloride, potassium sulfate, potassium phosphate, ammonium chloride, calcium chloride, magnesium chloride, magnesium sulfate, calcium sulfate and ammonium sulfate.

4. A feedstock in accordance with claim 1 wherein the magnesium ingredient comprises magnesium oxide and/or magnesium hydroxide.

5. A feedstock in accordance with claim 1 wherein the omega-6 fatty acid nutrient is in the form of calcium salt and/or magnesium salt, and/or amide derivative.

6. A feedstock in accordance with claim 1 wherein the omega-6 fatty acid nutrient is linoleic acid and/or arachidonic acid derivative.

7. A dietary supplement for incorporation in ruminant feedstock for control of hypocalcemia in prepartum dairy cattle, wherein the supplement is formulated to provide macromineral cations and anions and omega-6 fatty acid derivative in calculated proportions in a basal ration, whereby the resultant macromineral and omega-6 fatty acid derivative specifications meet the requirements of a feedstock in accordance with claim 1.

8. A dietary supplement adapted for incorporation in ruminant feedstock for control of hypocalcemia in prepartum dairy cattle, wherein the supplement is formulated to provide macromineral cations and anions and omega-6 fatty acid derivative having rumen-bypass properties, and wherein the supplement comprises the following parts by weight of ingredients:

| | |
|---|---|
| Chloride-containing | 10–30 |
| Sulfur-containing | 0–50 |
| Magnesium-containing | 5–30 |
| Omega-6 fatty acid derivative-containing. | 50–120 |

9. A dietary supplement in accordance with claim 8 having a content comprising the following parts by weight of ingredients:

| | |
|---|---|
| Calcium chloride | 10–30 |
| Magnesium sulfate | 5–30 |
| Linoleic acid amide arachidonic acid amide and combinations thereof. | 50–120 |

10. A dietary supplement in accordance with claim 8 having a content comprising the following parts by weight of ingredients:

| | |
|---|---|
| Calcium chloride | 10–30 |
| Magnesium sulfate | 5–30 |
| Calcium salt magnesium salt of linoleic acid and arachidonic acid and combinations thereof. | 50–120 |

11. A method for controlling hypocalcemia in prepartum dairy cattle which comprises feeding a prepartum cow with a feedstock comprising a supplemented basal ration having a prescribed content of nutrients comprising (1) macromineral proportions as defined by a dietary cation-anion difference (DCAD) which corresponds to the equation:

$$DCAD = meq(Na^+ + K^+) - (Cl^- + SO_4^{-2})/100 \text{ g dietary } DM$$

where meq is milliequivalents, Na is sodium cations, K is potassium cations, Cl is chloride anions, $SO_4$ is sulfate anions, and DM is dry matter; wherein DCAD has a value between about −5 and +20 meq/100 g dietary DM; and wherein the feedstock has a weight ratio of potassium:magnesium between about 3-5:1; and (2) between about 1-12 g/kg dietary DM of omega-6 fatty acid derivative having rumen-bypass properties.

12. A method in accordance with claim 11 wherein the DCAD macrominerals are selected from the group consisting of sodium bicarbonate, sodium carbonate, sodium sesquicarbonate, sodium chloride, sodium sulfate, sodium phosphate, potassium bicarbonate, potassium carbonate, potassium chloride, potassium sulfate, potassium phosphate, ammonium chloride, calcium chloride, magnesium chloride, magnesium sulfate, calcium sulfate and ammonium sulfate.

13. A method in accordance with claim 11 wherein the magnesium nutrient comprises magnesium oxide and/or magnesium hydroxide.

14. A method in accordance with claim 11 wherein the omega-6 fatty acid nutrient is in the form of calcium salt and/or magnesium salt and/or amide derivative.

15. A method in accordance with claim 11 wherein the omega-6 fatty acid nutrient is linoleic acid/or arachidonic acid derivative.

16. A method in accordance with claim 11 wherein the rate of feeding is between about 8-12 kg DM/cow/day.

17. A method in accordance with claim 11 wherein the rate of feeding provides between about 20-100 g/cow/day of rumen-bypass omega-6 fatty acid derivative in the cow intestine.

18. A method in accordance with claim 11 wherein the rate of feeding provides between about 20-100 g/cow/day of rumen-bypass linoleic acid and/or arachidonic acid derivative in the cow intestine.

* * * * *